US00PP20439P3

(12) United States Plant Patent
Barfield

(10) Patent No.: US PP20,439 P3
(45) Date of Patent: Oct. 27, 2009

(54) EXOTIC ORCHID 'GOLDEN GAMBOL'

(50) Latin Name: *Maclellanara*
Varietal Denomination: Golden Gambol

(76) Inventor: Robert Glen Barfield, P.O. Box 355, Hakalau, HI (US) 96710

( * ) Notice: Subject to any disclaimer, the term of this patent is extended or adjusted under 35 U.S.C. 154(b) by 0 days.

(21) Appl. No.: 11/974,400

(22) Filed: Oct. 15, 2007

(65) Prior Publication Data

US 2009/0119813 P1 May 7, 2009

(51) Int. Cl.
*A01H 5/00* (2006.01)

(52) U.S. Cl. ..... Plt./311

(58) Field of Classification Search ..... Plt./311
See application file for complete search history.

*Primary Examiner*—Annette H Para

(57) ABSTRACT

A new variety of orchid plant of the Oncidiinae Intergeneric group, of the *Maclellanara nothogenera*, named EXOTIC ORCHID 'Golden Gambol', distinguished in part by a rich butter yellow background, highly contrasted with chocolate blotching, and growing without cultural issues from in-vitro culture to in-vivo flowering. EXOTIC ORCHID 'Golden Gambol' grows very fast to sexual maturity and flowers freely.

2 Drawing Sheets

Latin name of the genus and grex fo the plant claimed:

The Latin name of the genus and grex of the plant claimed is *Maclellanara*Yellow Star 'Golden Gambol' to be identified in the trade as, EXOTIC ORCHID 'Golden Gambol'.

Variety denomination:

The present invention comprises a new and distinct cultivar of *Oncidiinae* orchid, and hereinafter referred to by the cultivar name EXOTIC ORCHID 'Golden Gambol'.

BACKGROUND OF THE INVENTION

*Oncidiinae* comprises several genera with approximately 2,000 species from the tropical and subtropical Americas. *Oncidiinae* are primarily epiphytic or lithophytic with a minor portion being terrestrial. All species are sympodial in growth and may vary greatly in other morphology and size.

*Oncidiinae* breeding is typically done by sexual methods. Asexual propagation of *Oncidiinae* is often done in aseptic tissue culture from apical and/or axillary shoots.

The new cultivar was discovered within the progeny of a cross made by Mauna Kea Orchids in March 2000. EXOTIC ORCHID 'Golden Gambol' was flowered, re-flowered and evaluated. Because of its unique color, different from both parents and siblings, and its rapid growth to sexual maturity, was determined to be worthy of production and protection. EXOTIC ORCHID 'Golden Gambol' was submitted by the discoverer to a commercial laboratory in Bangkok, Thailand on Dec. 4, 2004, for propagation through aseptic tissue culture technique. A quantity was produced for evaluation and has demonstrated that the unique combination of characteristics as herein disclosed for the new cultivar are firmly fixed and are retained through one generation of asexual reproduction.

BRIEF SUMMARY OF THE INVENTION

The following traits have been repeatedly observed and are determined to be basic characteristics of the new cultivar which in combination distinguish this *Maclellanara* orchid as a new and distinct cultivar.

Flowers of the new cultivar are star shaped with medium yellow sepals and petals with intermittent dark chocolate brown colored blotches centrally. The labellum is yellow with dark chocolate brown flecking centrally. The horizontal natural spread is 10.7 centimeters and the vertical spread is 11.2 centimeters.

Inflorescence is primarily produces a basal spike, approximately 70 centimeters tall with 16 flowers on a first bloom plant. This plant has occasionally produced an apical spice with 3 to 4 flowers. There are generally 4 leaves on a mature pseudobulb, 2 from the base and 2 from the apex. They range in length from 2.7 to 7 centimeters in width and 12.5 to 39.5 centimeters in length.

Plants of the new cultivar have not been observed under all possible environmental conditions. The phenotype may vary with variations in the environment such as temperature, light intensity, day length and nutrition, without any change in the genotype.

Plants of the new cultivar differ primarily from plants of the parent cultivars in flower color, flower size, inflorescence size, overall plant size, rate of growth, and speed to sexual maturity. Perhaps the closest commercial comparison to the new cultivar can be made to one of its parents, Brassidium Gilded Urchin 'Ontario'. Principle differences between Brassidium Gilded Urchin 'Ontario' and EXOTIC ORCHID 'Golden Gambol' are flower color, tepal width and time to sexual maturity. All three of these differences show EXOTIC ORCHID 'Golden Gambol' to be superior. Other commercial comparisons would be of other *Oncidiinae* seedling orchids of the same grex that are genetically heterogeneous, and typically lack uniformity in growth, vigor, plant habit, speed to sexual maturity and flower quality. Since this reference point has inconsistent characteristics, a direct comparison for EXOTIC ORCHID 'Golden Gambol' other than Brassidium Gilded Urchin 'Ontario' is not available. The new cultivar is a single genotype asexually propagated via tissue culture; thus, its combined horticultural characteristics mentioned above are uniform and predictable.

EXOTIC ORCHID 'Golden Gambol' may be tissue cultured via aseptic axillary shoot multiplication. This method has been proven to produce identical plants for production at an economical cost.

DESCRIPTION OF THE DRAWINGS

All color references are measured against the Pantone® Color System. Colors and numerical measurements are approximate as plant growth, development and flower qualities depend on environmental conditions and cultural practices such as light, temperature, water, nutrition, among others, and may vary without any variance in the genotype.

Plants used for this description are 1½ to 2 years in-vivo and grown in 72 cell plug trays for 8 months and then in 3.5 inch square plastic pots to flowering which occurred approximately 12 months after planting. The plants were grown in a poly-carbonate covered greenhouse near Hakalau, Hi., where day temperatures range from 73 to 88 degrees Fahrenheit and night temperatures range from 62 to 75 degrees Fahrenheit. Light levels are between 1,500 and 2,500 foot candles. This information reflects the annual variations for the area.

FIG. 1 (one) demonstrates the spike habit if not staked to present an upright display. FIG. 2 (two) demonstrates the patterns, markings, spacing and colors of the flowers.

DETAILED BOTANICAL DESCRIPTION

Botanical classification:

Name: *Maclellanara* Yellow Star 'Golden Gambol '

Parentage:

*Seed parent.*—Brassidium Gilded Urchin 'Ontario'.

*Pollen parent.*—Odontioda Cornelia 'Distinctive'.

Propagation:

*Type.*—Asexual propagation by aseptic tissue culture axillary shoot initiation.

*Time to initiate and elongate shoots in-vitro.*—About 280 days.

*Time to produce fully rooted young plants in vitro.*—About 420 days.

Plant description:

Under appropriate growing conditions, plants of the new cultivar attain a mature size of about 32 centimeters in height (top of leaf plane) and about 25 centimeters in width.

Root description:

White with green growing tip and thick velum covering approximately 2 millimeters in diameter.

Foliage description:

*Arrangement.*—Sympodial growth habit.

*Quantity of leaves per sympodial growth.*—4.

*Leaf dimensions.*—The apical leaves are from 32.5 to 39.5 centimeters in length and are from 4.6 to 7 centimeters wide. The basal leaves are from 12.5 to 22 centimeters long and from 2.7 to 4 centimeters wide.

*Leaf shape.*—The shape is subulate and lanceolate. The texture and substance is smooth, waxy and thin.

*Pseudobulb shape.*—The pseudobulb is a laterally compressed ovoid.

*Pseudobulb length.*—Twelve to 14 centimeters long and 5 to 6 centimeters wide.

*Foliage color.*—The foliage color, both top and bottom of the leaf, is Pantone® 370 C (green). The pseudobulbs are Pantone® 370° C (green) as well. The colors are consistent with no contrasting venation, blotching or gradient noted.

*Inflorescence description.*—Inflorescence is a basal spike, approximately 68 centimeters long with approximately 16 flowers on the first bloom.

*Flower arrangement description.*—The flowers are arranged with every other flower facing the opposite direction.

*Flower description.*—Flowers of the new cultivar are star shaped with yellow sepals and petals with central dark chocolate brown blotches. The labellum is yellow with dark chocolate brown flecking. The horizontal natural spread is 10.7 centimeters and the vertical spread is 11.2.

*Flower dimensions.*—Sepals are 1.6 centimeters wide and 5.7 centimeters long. Petals are 1.9 centimeters wide and 4.9 centimeters long. The labellum is 2.5 centimeters wide and 7 centimeters long.

*Flower coloration.*—The sepals and petals are Pantone® 1215° C. (yellow) with central blotching of Pantone® 4705° C. (brown). The labellum is Pantone® 1215° C. (yellow) with Pantone® 4705° (brown) spots centrally and the crest is Pantone® 107° C. (yellow).

*Flower quantity on first bloom plant.*—Sixteen flowers.

*Flower longevity.*—Five to 6 weeks in favorable conditions.

*Flowering season.*—EXOTIC ORCHID 'Golden Gambol' does not seem to have a flowering season. When a growth matures, it flowers. Flowering has occurred at about 9 month intervals once the plant has reached maturity.

*Fragrance.*—EXOTIC ORCHID 'Golden Gambol' has not been recognized as having a fragrance.

Reproductive organs: The stamens, style and stigmas are fused into a single short structure referred to as the column, possessing one terminal anther with pollen grains united to pollinia, which are covered by an anther cap. The stigma is located under the column behind the pollinia. The ovary is inferior, with 3 carpels being present.

*Column.*—The column is erect with wings on either side of the stigma, 2.2 millimeters wide and 4.6 millimeters long.

*Pollinia.*—Two oval masses of pollen are present, about 1.6 millimeters in diameter. The bright yellow color darkens with age.

*Stigma.*—The stigma is concave, oval, with high gloss, and sticky.

*Ovary.*—The ovary is about 3.6 centimeters long and 6 millimeters in diameter.

*Seed.*—Seed production has not been observed.

Disease resistance: The cultivar shows little disease in the commercial production environment, but resistance to know pathogens of *Oncidiinae* has not been tested or observed on plants grown under commercial production conditions.

General observations: Plants of EXOTIC ORCHID 'Golden Gambol' produce a pleasing arrangement of many flowers held on a semi erect spike. The flowers are long lasting and the plant grows well without cultural or disease issues to maturity and blooms at a young age on the third pseudobulb. At the nursery location in Hakalau, Hi. that first flowering occurred approximately 20 months after being transferred from in-vitro to in-vivo.

What is claimed is:

1. A new and distinct variety of orchid plant named EXOTIC ORCHID 'Golden Gambol', substantially as illustrated and described herein.

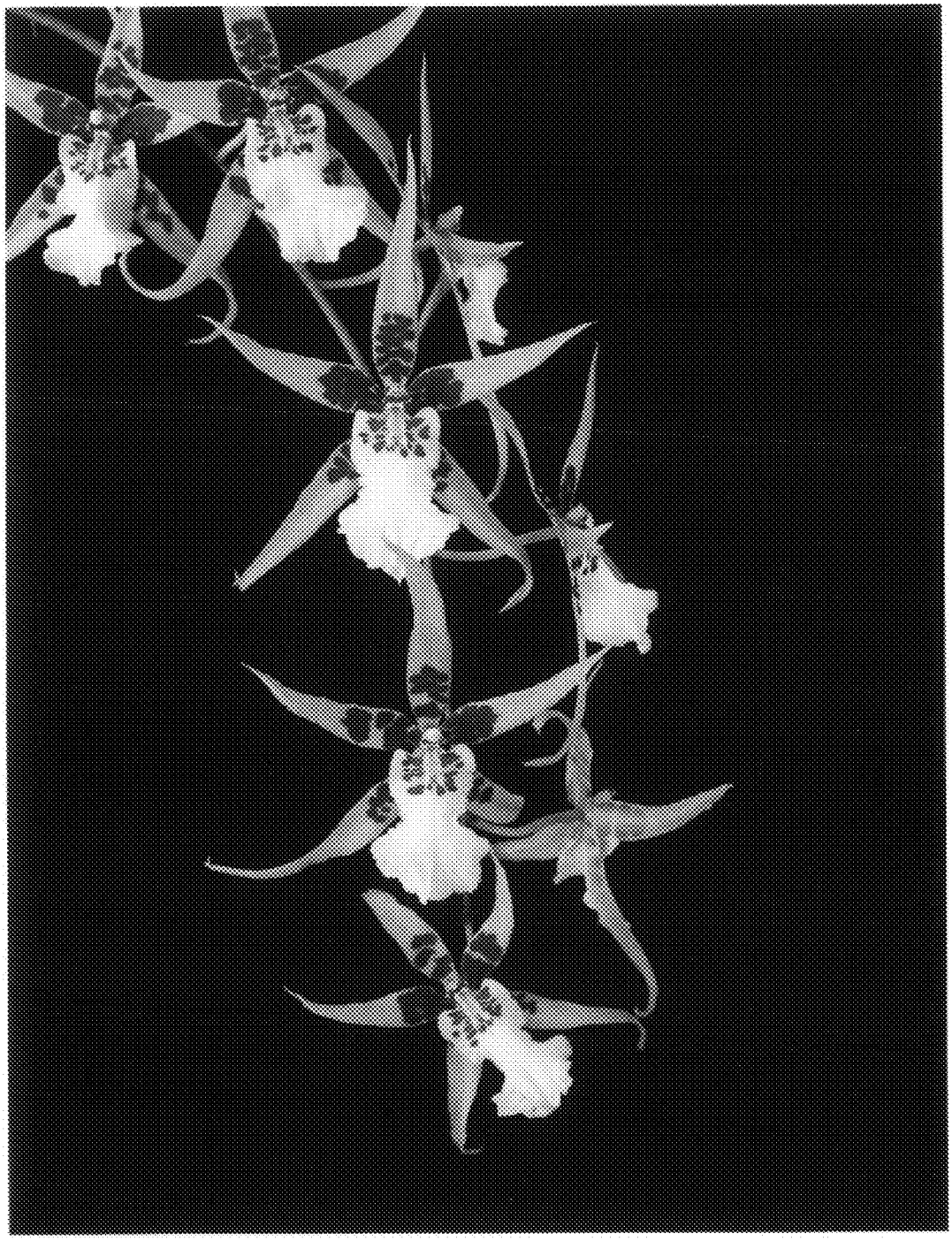

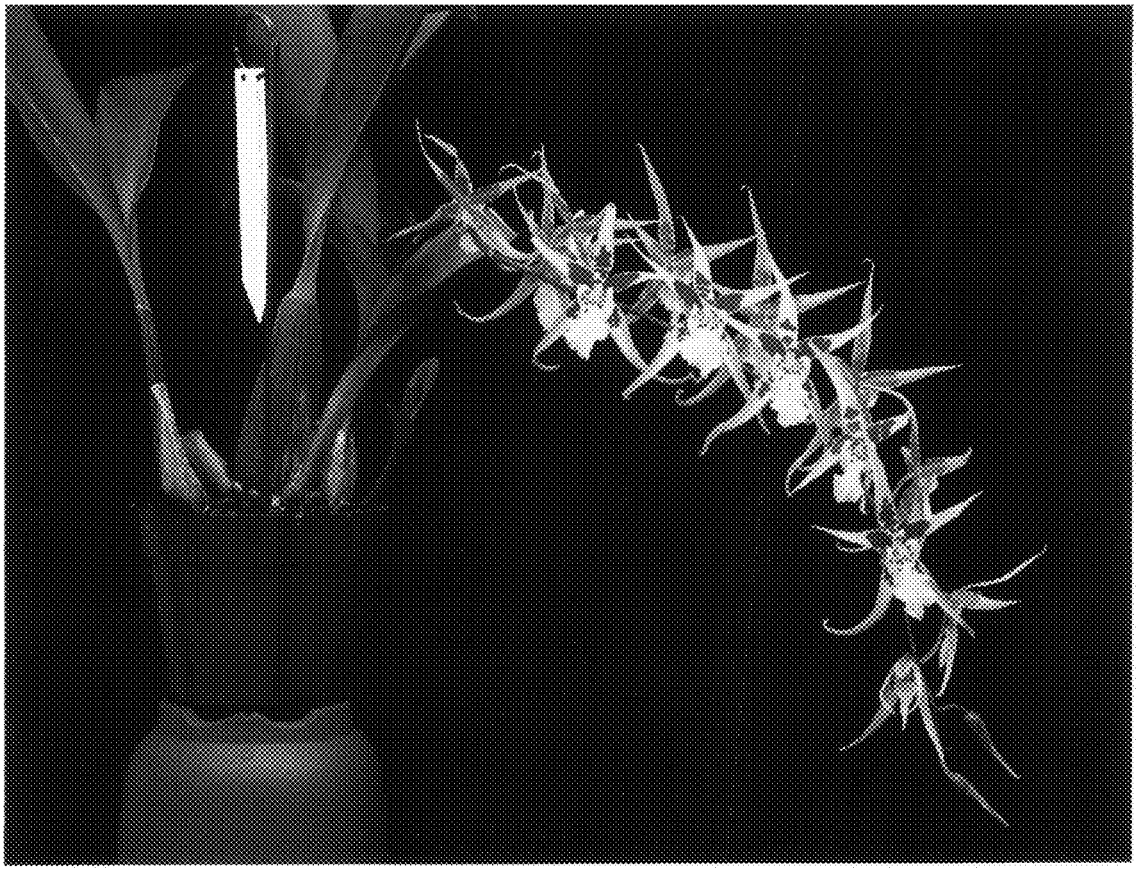

* * * * *